United States Patent [19]

Scherowsky et al.

[11] Patent Number: 5,651,918
[45] Date of Patent: Jul. 29, 1997

[54] OPTICALLY ACTIVE 1,3-DIOXOLANE DERIVATIVES CARRYING A MESOGENIC RADICAL IN THE 4-POSITION, A PROCESS FOR THEIR PREPARATION AND THEIR USE AS DOPING AGENTS IN LIQUID-CRYSTAL MIXTURES

[75] Inventors: Günter Scherowsky; Jürgen Gay, both of Berlin; Rainer Wingen, Hattersheim am Main; Hans-Rolf Dübal, Königstein/Taunus; Claus Escher, Mühltal; Wolfgang Hemmerling, Sulzbach, all of Germany; Yoshio Inoguchi, Tokyo, Japan; Ingrid Müller, Hofheim am Taunus; Dieter Ohlendorf, Liederbach, both of Germany

[73] Assignee: Hoechst Aktiengesellschaft, Frankfurt, Germany

[21] Appl. No.: 454,059

[22] Filed: May 30, 1995

Related U.S. Application Data

[63] Continuation of Ser. No. 208,727, Mar. 9, 1994, abandoned, which is a continuation of Ser. No. 879,698, May 5, 1992, abandoned, which is a continuation of Ser. No. 383,320, Jul. 20, 1989, abandoned.

[30] Foreign Application Priority Data

Jul. 22, 1988 [DE] Germany ............ 38 24 902.2

[51] Int. Cl.$^6$ ...................................... C09K 19/34
[52] U.S. Cl. ...................................... 252/299.61
[58] Field of Search ........................... 252/299.61

[56] References Cited

U.S. PATENT DOCUMENTS

| | | |
|---|---|---|
| 4,322,354 | 3/1982 | Sorkin . |
| 4,424,372 | 1/1984 | Hsu . |
| 4,873,019 | 10/1989 | Krause et al. . |
| 5,288,425 | 2/1994 | Scherowsky et al. . |
| 5,328,638 | 7/1994 | Muller et al. ............ 252/299.61 |
| 5,445,763 | 8/1995 | Schlosser et al. ........ 252/299.61 |

FOREIGN PATENT DOCUMENTS

| | | |
|---|---|---|
| 0234437 | 9/1987 | European Pat. Off. . |
| 0288813 | 11/1988 | European Pat. Off. . |
| 0306195 | 3/1989 | European Pat. Off. . |
| 3604899 | 8/1987 | Germany . |
| 3739588 | 7/1988 | Germany . |

OTHER PUBLICATIONS

Chemical Abstracts, 96(26): 218245n (Jun. 28, 1982).
Chemical Abstracts, 107(12): 106508q (Sep. 21, 1987).

*Primary Examiner*—Cynthia Harris Kelly
*Attorney, Agent, or Firm*—Curtis, Morris & Safford, P.C.

[57] ABSTRACT

Optically active 1,3-dioxolane derivatives which carry a mesogenic radical in the 4-position and have the general formula (I)

$$R^1\text{-}(A^1)_j\text{-}(M^1)_k\text{-}(A^2)_l\text{-}(M^2)_m\text{-}(A^3)_n\text{-}X\text{-}CH_2-\underset{R^4}{\overset{O}{\underset{|}{\diagup}}}\overset{R^2}{\underset{R^3}{\diagdown}} \quad (I)$$

are suitable for use as doping agents in liquid-crystal mixtures—in particular ferroelectric liquid-crystal mixtures. The symbols in the general formula have the following meanings:

$R^1$ is composed analogously to the part of the general formula on the right-hand side of X or is an alkyl or alkylene radical which can be substituted, $R^2$, $R_3$ and $R^4$ are H or alkyl ($R^4$ is also alkenyl) which can also be substituted [$R^2$ and $R^3$, together with the C(2) of the dioxolane ring are also a cycloaliphatic radical or a keto group], J, l and n are zero, 1 or 2 and k and m are zero or 1, subject to the proviso that, if k is zero n is zero and if n is zero m is zero and $1 \leq J+l+n \leq 3$, —$A^1$, —$A^2$ and —$A^3$ are an aromatic, heterocyclic or aliphatic ring system, —$M^1$ and —$M^2$ are —CO—O, —O—CO, —$CH_2CH_2$, —CH=CH, —$CH_2O$, —$OCH_2$ or —C≡C and X is O, S or O—CO—O.

6 Claims, No Drawings

OPTICALLY ACTIVE 1,3-DIOXOLANE DERIVATIVES CARRYING A MESOGENIC RADICAL IN THE 4-POSITION, A PROCESS FOR THEIR PREPARATION AND THEIR USE AS DOPING AGENTS IN LIQUID-CRYSTAL MIXTURES

This application is a continuation of abandoned application Ser. No. 08/208,727, filed on Mar. 9, 1994, which is a continuation of Ser. No. 07/879,698, filed on May 5, 1992, now abandoned, which is a continuation of Ser. No. 07/383,320, filed Jul. 20, 1989, now abandoned.

Particularly in the last decade, liquid crystals have found favor in various technical fields in which there is a demand for electrooptical properties and display device properties (for example in displays for clocks, pocket calculators and typewriters). These display devices are based on the dielectric orientation effects in the nematic, cholesteric and smectic phases of the liquid-crystals compounds, the molecular longitudinal axis of the compounds taking up—as a result of the dielectric anisotropy—a preferred orientation in an applied electric field. The usual switching times in the case of these display devices are rather too long for many other potential fields of use for liquid crystals, which in themselves are very promising chemical compounds for technology, owing to their unique properties. This disadvantage makes itself noticeable particularly when a large number of scanning elements have to be controlled, as a result of which the manufacturing costs of appliances containing fairly large areas, for example video appliances, oscillographs or television, radar, EDP or word processor screens, become excessively high.

In addition to the nematic and cholesteric liquid crystals, optically active, smectic liquid-crystal phases have also become of importance to an increasing extent in the last few years.

Clark and Lagerwall have been able to show that the use of ferroelectric liquid-crystal systems in very thin cells results in opto-electrical switching or display elements which have switching times that are faster by a factor of up to 1000 than those of the conventional TN (twisted nematic) cells (cf., for example, Lagerwall et al. "Ferroelectric Liquid Crystals for Displays", SID Symposium, October Meeting 1985, San Diego, Calif., USA). By virtue of these and other advantageous properties, for example the bi-stable switching ability and a contrast virtually independent of the angle of view, ferroelectric liquid crystals are, in principle, very suitable for the fields of use mentioned above, for example via a matrix control. This either requires compounds which form tilted-smectic phases and are themselves optically active, or it is possible to induce chiral, tilted-smectic phases by using optically active compounds to dope compounds which, although they form smectic phases of this type, are not themselves optically active. In this regard the desired phase should be stable over as wide as possible a temperature range.

A uniform, planar orientation of the liquid crystals is necessary to achieve a good contrast ratio in electro-optical structural elements. A good orientation in the $S_A^*$ and $S_C^*$ phases can be obtained if the phase sequence of the liquid-crystal mixture at a decreasing temperature is as follows:

$$\text{Isotropic} \rightarrow N^* \rightarrow S_A^* \rightarrow S_C^*.$$

It is a precondition that the pitch of the helix in the N* phase is very large (>10 μm) or, even better, is completely compensated. (T. Matsumoto et al., p. 468–470, Proc. of the 6th Int. Display Research Conf., Japan Display, Sep. 30–Oct. 2, 1986, Tokyo, Japan; M. Murakami et al., ibid. p. 344–p. 347). This is achieved by adding to the chiral liquid-crystal mixture containing, for example, a left-handed helix in the N* phase, a sufficient amount of another optically active doping substance which induces a right-handed helix for the helix to be exactly or at least approximately (pitch>10 μm) compensated.

Although compounds are already known from the state of the art which have some of the properties described above, a broad selection of doping substances is required since the preparation of liquid-crystal mixtures suitable for industry—depending on the nature and number of the components—is a highly complex procedure. Compounds which are particularly desired are those which have a high twisting power when added in small mounts and which effect the compensation described above without at the same time having a harmful effect on the other properties of the mixtures (for example a high spontaneous polarization $P_s$) which are desired and are therefore "included amongst the components". The object of the present invention is, therefore, to synthesize new compounds which have these properties and which are compatible with a very wide variety of liquid-crystal mixtures.

The invention relates to optically active 1,3-dioxolane derivatives which carry a mesogenic radical in the 4-position and have the general formula (I)

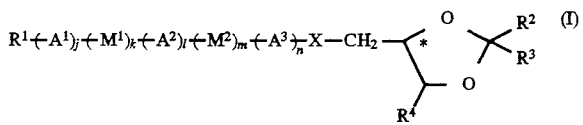

in which the symbols have the following meanings:

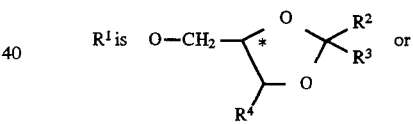

a linear or branched alkyl radical having 1 to 16 carbon atoms or a linear or branched alkenyl radical having 3 to 16 carbon atoms, it being possible for these radicals themselves to contain asymmetric carbon atoms and for one or more non-adjacent —$CH_2$— groups to be replaced by —O—, —S—, —CO—, —O—CO— and/or —CO—O—, and for one or more H atoms to be replaced by F, Cl, Br or CN, $R^2$ and $R^3$ are each H or an alkyl radical having 1 to 10 carbon atoms, it being possible for one or more H atoms of the alkyl groups to be replaced by F, or $R^2$ and $R^3$, together with the C(2) atom of the dioxolane ring, form a cyclopentane, cyclohexane or cycloheptane ring or a keto group, $R^4$ is H or an alkyl radical having 1 to 10 carbon atoms or an alkenyl radical having 2 to 10 carbon atoms, j and l are zero, 1 or 2, k and m are zero or 1, n is zero, 1 or 2, subject to the following proviso: if j and/or l are zero, k is zero; if n is zero, m is zero; the total j+l+n is not less than 1 and not more than 3, —A¹ and —A² are

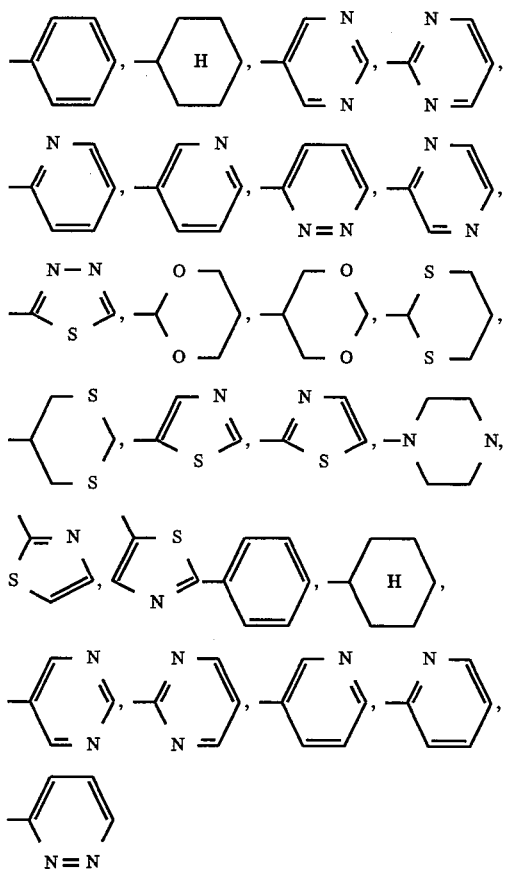

—M¹ and —M² are —CO—O, —O—CO, —CH₂CH₂, —CH=CH, —CH₂O, —OCH₂ or —C≡C and
X is O, S or O—CO—O.

The above formulae are to be understood in such a way that the nearest group is adjacent to the extreme right-hand part of the molecule.

In a preferred embodiment the symbols in the general formula (I) have the following meanings:

R¹ is a linear or branched alkyl or alkenyl radical which has 4 to 14 carbon atoms and which can contain an asymmetric carbon atom, or in which a —CH₂— group can be replaced by —O—, —S— or —O—CO—, or in which one or more H atoms can be replaced by F, R², R³ and R⁴ are H or an alkyl radical having 1 to 5 carbon atoms, or R² and R³, together with the C(2) atom of the dioxolane ring, are a cyclopentane or cyclohexane ring or a keto group, j and l are zero or 1, k, m and n are zero or 1, —M¹ and —M² are —CO—O or —O—CO and
X is O or O—CO—O.

In another preferred embodiment the 1,3-dioxolane derivatives have the general formula (IV)

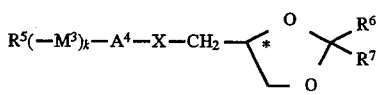

in which

R⁶ and R⁷ denote methyl or, together with the C(2) atom of the dioxolane ring, denote a cyclohexane ring.

R⁵ denotes a linear or branched alkyl or alkenyl radical which has 6 to 12 carbon atoms and which can contain an asymmetric carbon atom, —M³ denotes —O, —S or —O—CO and —A⁴ denotes

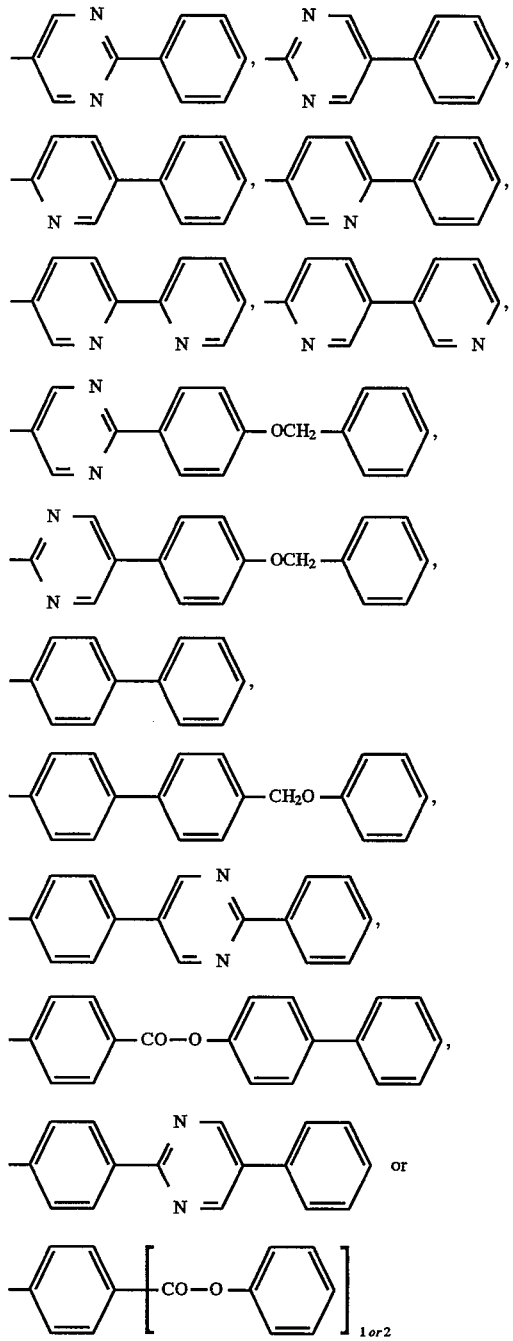

The new compounds of the general formula I, in particular (IV), preferably include the compounds mentioned by name in the examples.

The compounds of the general formula (I) are prepared by reacting mesogenic phenols, thiophenols or carbonic acid monoesters of the general formula (II)

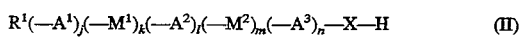

(II)

with suitable derivatives of the 1,3-dioxolane (III)

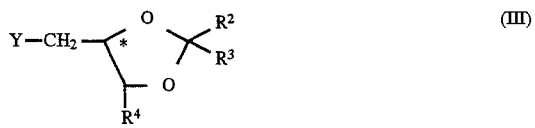

in which Y represents a typical leaving group.

Thus compounds in which X=O in (II) and Y=OH in (III) can be reacted in the presence of azodicarboxylic acid diester and triphenylphosphine to give (I); this is an application of a method known to those skilled in the art as the Mitsunobo Reaction (see, for example, J. Chem. Soc. Perkin Trans 1975, 461). It is also possible, however, to react with (III) alkali metal salts or alkaline earth metal salts derived from (II) in which Y represents a typical leaving group, such as methylsulfonyl, trifluoromethylsulfonyl, 4-toluenesulfonyl or another leaving group known to those skilled in the art (from the standard literature on nucleophilic substitution reactions).

Methods for the preparation of compounds of the type (II) are known to those skilled in the art (for example Zaschke et al., Flüssige Kristalle in Tabellen ("Liquid Crystals in Tables"), volumes I and II, . . . ); the carbonic acid monoesters of the type (II), for example, are prepared from the corresponding phenols and phosgene in the presence of an organic base.

In general, the compounds (III) are commercially available or can be prepared in accordance with literature references, such as Tetrahedron 42, 447 (1986). The compounds (I) can, as a rule, be purified by chromatography and/or crystallization.

The liquid-crystal mixtures, in particular ferroelectric liquid-crystal mixtures, constituting another means of achieving the stated object form liquid-crystal phases and contain at least one optically active compound of the general formula (I).

The term "liquid-crystal phase" is to be understood as meaning nematic, cholesteric, orthogonally smectic or tilted smectic phases, in particular $S_c^*$ phases. The liquid-crystal mixtures are composed of 2 to 20, preferably ably 2 to 15, components, including at least one of the chiral compounds claimed in accordance with the invention.

The other constituents are preferably selected from the known compounds which have nematic, cholesteric and/or smectic phases; these include, for example, Schiff's bases, biphenyls, terphenyls, phenylcyclohexanes, cyclohexylbiphenyls, heterocyclic compounds containing N, S or O, for example pyrimidines, cinnamic acid esters, cholesterol esters or polynuclear esters of p-alkylbenzoic acids which are bridged in various ways and contain terminal polar groups. In general, the commercially available liquid-crystal mixtures are already, before the addition of the optically active compound(s), in the form of mixtures of a very wide variety of components at least one of which is mesogenic, i.e. exhibits, as the compound, in the form of derivatives or when mixed with certain co-components, a liquid-crystal phase which can be expected to format least one enantiotropic meso phase (clear point>melting point) or monotropic meso phase (clear point<melting point).

In particular, the liquid-crystal mixture contains, as well as at least one of the optically active compounds claimed in accordance with the invention, an ester compound having an $S_c$ phase, for example a phenyl alkoxybenzoate, or a biaromatic compound having a heterocyclic radical containing nitrogen, for example an alkylpyrimidinylalkoxybenzene.

In general, the liquid-crystal mixtures contain 0.05 to 70% by weight, in particular 0.1 to 50% by weight, of the compound(s) according to the invention.

The compounds according to the invention are suitable for use as doping agents for liquid-crystal mixtures—in particular ferroelectric liquid-crystal mixtures—having nematic, cholesteric and/or smectic phases. In nematic and/or cholesteric phases, for example, they exhibit a high twisting power, even small added amounts being adequate to perform the helix compensation described at the outset, without having an essentially unfavorable effect on other, already existing, properties of the doped mixture. A highly specific effectiveness of this type is extremely advantageous in the development of mixtures suitable for industry.

In particular, the compounds according to the invention produce only a slight spontaneous polarization $P_s$ in $S_c$ phases, so that, although they affect the pitch of a mixture greatly, they hardly affect the polarization. The compounds are therefore preferably suitable for use in ferroelectric mixtures irrespective of the sign of the spontaneous polarization existing there [for example R. B. Meyer et al., J. Phys. (Paris) Lett. 36 L-69 (1975)]. The compounds according to the invention also induce a helix in the $S_c$ phase, so that this effect can be made use of in order to compensate for twisting in the $S_c^*$ phase or to adjust it to a specific value, which is advantageous for use in practice [for example T. Tsuchiga et al., Jpn. J. Appl. Phys. 25, L-27 (1986)].

The high twisting power of the compounds according to the invention results, even in nematic phases, to advantageous opportunities for use in the somewhat "classical" display technologies. In this case, however, the principle factor is often not compensation but achieving twisting by adding the smallest possible amount of chiral doping agent. This applies to both the TN (twisted-nematic) technology which at the present time (still) dominates the market [M. Schadt et al., Appl. Phys. Lett 18, 127 (1971)] and to the so-called White-Taylor display [D. L. White et al., J. Appl. Phys. 45, 4718 (1974)] or the SBE/STN (super-birefringence-effect/super-twisted-nematic) display [T. J. Scheffer et al., Appl. Phys. Lett. 45, 1021 (1984)] and its various modifications such as the OMI (optical mode interference) display [M. Schadt et al., Appl. Phys. Lett. 50, 236 (1987)].

EXAMPLE 1

(S)-4-(5-Octylpyrimidin-2-yl)-phenyl (2,2-dimethyl-1,3-dioxolan-4-yl)-methyl ether

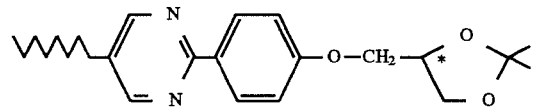

0.83 ml of diethyl azodicarboxylate is added at 0° C. to a solution of 1.38 g of triphenylphosphine in 30 ml of tetrahydrofuran. After 15 minutes 1.5 g of 4-(5-octylpyrimidin-2-yl)-phenol and 0.7 g of (S)-2,2-dimethyl-1,3-dioxolane-4-methanol are added and the mixture is kept at 25° C. for 2 days. The solvent is removed by distillation and the residue is separated by chromatography (SiO$_2$, 95/5 CH$_2$Cl$_2$/ethyl acetate). 0.95 g of the desired product, which has a melting point of 114.2° C., is obtained after recrystallization from n-hexane.

$[\alpha]_D^{22}$:+6.6 (c=5, CHCl$_3$)

The following are obtained analogously:

EXAMPLE 2

(S)-4-(2-Octyloxypyrimidin-5-yl)-phenyl (2,2-dimethyl-1,3-dioxolan-4-yl)-methyl ether

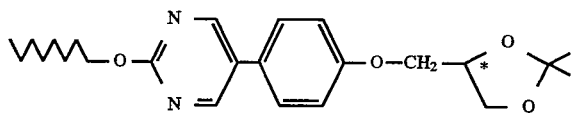

Melting point: 90.2° C. $[\alpha]_D^{22}$:+4.1 (c=5, CHCl$_3$)

EXAMPLE 3

(S)-4-(5-Octylthiopyrimidin-5-yl)-phenyl (2,2-dimethyl-1,3-dioxolan-4-yl)-methyl ether

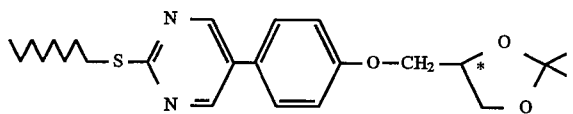

Melting point: 86.8° C. $[\alpha]_D^{22}$:+4.0 (c=5, CHCl$_3$)

EXAMPLE 4

(S)-4-(2-Octylpyrimidin-5-yl)-phenyl (2,2-dimethyl-1,3-dioxolan-4-yl)-methyl ether

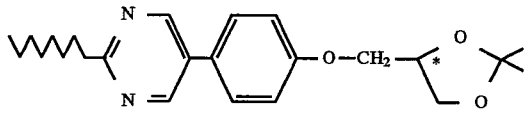

Melting point: 95.6° C. $[\alpha]_D^{22}$:+4.4 (c=5, CHCl$_3$)

EXAMPLE 5

(S)-4-(5-Octyloxypyrimidin-2-yl)-phenyl (2,2-dimethyl-1,3-dioxolan-4-yl)-methyl ether

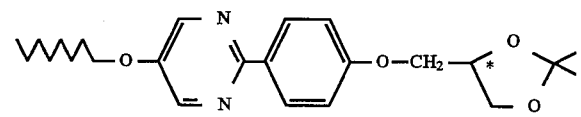

Melting point: 94.2° C. $[\alpha]_D^{22}$:+8.3 (c=5, CHCl$_3$)

EXAMPLE 6

(S)-4-[5-(4-Hexylphenyl)-pyrimidin-2-yl]-phenyl (2,2-dimethyl-1,3-dioxolan-4-yl)-methyl ether

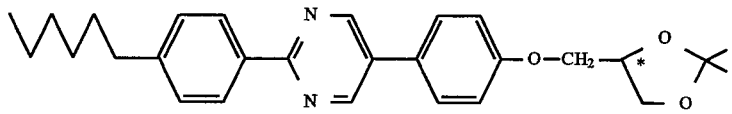

Melting point: 110° C. $[\alpha]_D^{22}$:+3.9 (c=5, CHCl$_3$) Clear point: 164° C.

EXAMPLE 7

(S)-4-(4-Decyloxybenzoyloxy)-phenyl (2,2-dimethyl-1,3-dioxolan-4-yl)-methyl ether

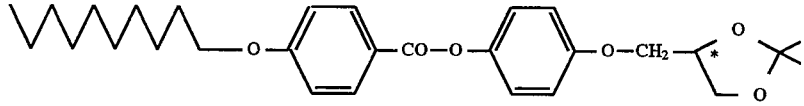

Melting point: 70.4° C. $[\alpha]_D^{22}$:+4.9 (c=5, CHCl$_3$)

EXAMPLE 8

(S)-[4-(4-Octyloxybenzoyloxy)-benzoyloxy]-phenyl (2,2-dimethyl-1,3-dioxolan-4-yl)-methyl ether

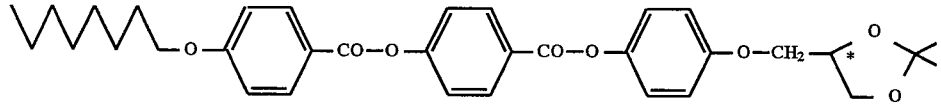

X 126 S$_A$* 149N* 175 I $[\alpha]_D^{22}$:+3.6 (C=5, CHCl$_3$)

This compound is itself liquid-crystal and can therefore —in addition to functioning as a chiral doping agent—also be employed for enlarging the $S_A^*$-phase and $N^*$-phase range of liquid-crystal mixtures.

EXAMPLE 9

(S)-4-[5-(1H,1H-Perfluorooctyloxy)-pyrimidin-2-yl]-phenyl (2,2-dimethyl-1,3-dioxolan-4-yl)-methyl ether

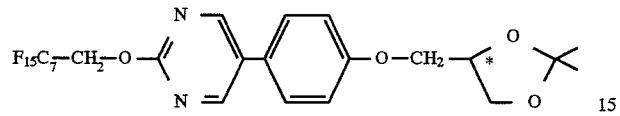

Melting point: 98.9° C. $[\alpha]_D^{22}$:+4.0 (c=5, CHCl$_3$)

EXAMPLE 10

(S)-4-[5-(7-Methylnonyloxy)-pyrimidin-2-yl]-phenyl (2,2-dimethyl-1,3-dioxolan-4-yl)-methyl ether

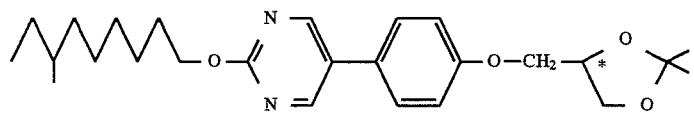

X 56 $S_A$ 57 I $[\alpha]_D^{22}$:+9.7 (c=5, CHCl$_3$)

The occurrence of an $S_A$ phase gives this compound particularly good compatibility in smectic phases.

The following are obtained analogously, but using (S)-2-oxo-1,3-dioxolane-4-methanol or the 5-propyl-4-methanol derivative:

EXAMPLE 11

(S)-4-(5-Octylpyrimidin-2-yl)-phenyl (2-oxo-1,3-dioxolan-4-yl)-methyl ether

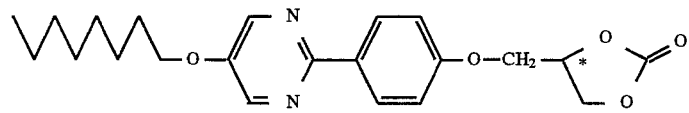

Melting point: 122.4° C. $[\alpha]_D^{22}$:−5.3 (c=5, CHCl$_3$)

EXAMPLE 12

(S)-4-(2-Octylthiopyrimidin-5-yl)-phenyl (2-oxo-1,3-dioxolan-4-yl)-methyl ether

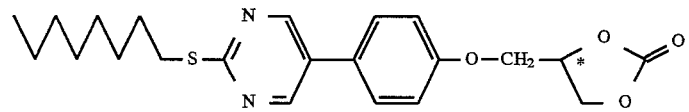

Melting point: 104.9° C. $[\alpha]_D^{22}$:−10.0 (c=5, CHCl$_3$)

EXAMPLE 13

(S)-4-(2-Octyloxypyrimidin-5-yl)-phenyl (2-oxo-1,3-dioxolan-4-yl)-methyl ether

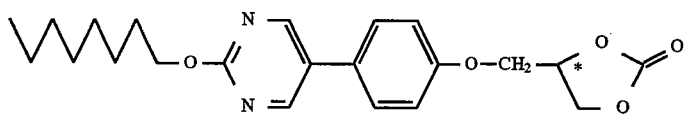

Melting point: 117.8° C. $[\alpha]_D^{22}$: −8.9 (c=5, CHCl$_3$)

EXAMPLE 14

4-Dodecyloxybiphenyl-4'-yl(2-oxo-5-propyl-1,3-dioxolan-4-yl)-methyl ether

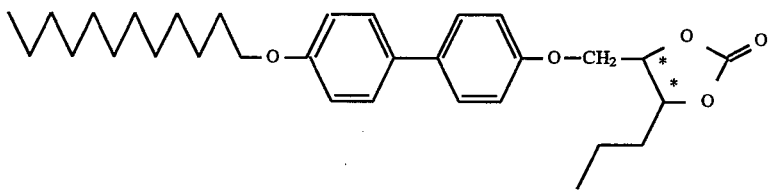

Melting point: 94° C.

EXAMPLE 15 cis-4-(4-Dodecyloxybenzoyloxy)-biphenyl-4'-yl (2-oxo-5-propyl-1,3-dioxolan-4-yl)-methyl ether

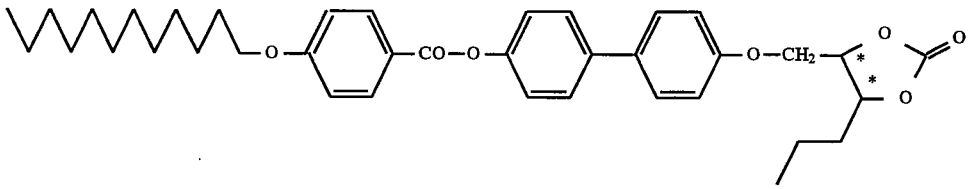

Melting point: 122.5° C.

EXAMPLE 16 trans-4-(4-Decyloxybenzoyloxy)-biphenyl-4'-yl (2-oxo-5-propyl-1,3-dioxolan-4-yl)-methyl ether

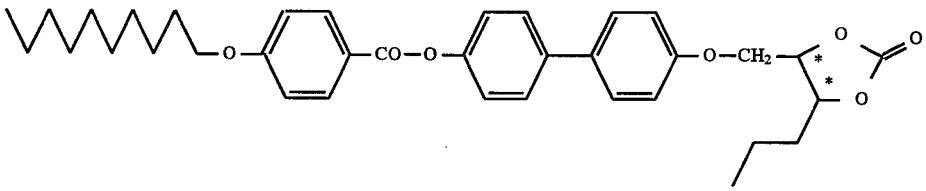

Phase sequence: K 133.5 S$_A$ 146.5 I

EXAMPLE 17 cis-[4-(5-Octyloxypyrimidin-2-yl)-phenyl](2-oxo-5-propyl-1,3-dioxolan-4-yl)-methyl ether

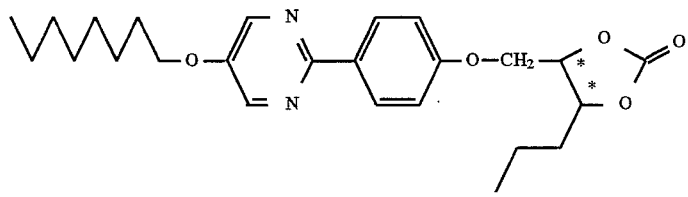

Melting point: 100° C.

EXAMPLE 18 trans-[4-(5-Octyloxypyrmidin-2-yl)-phenyl](2-oxo-5-propyl-1,3-dioxolan-4-yl)-methyl ether

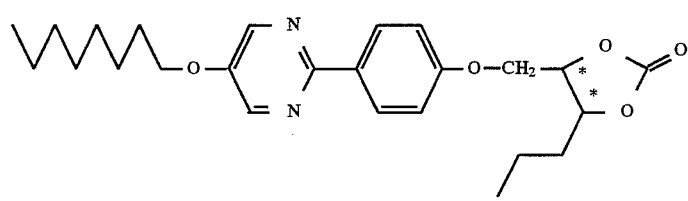

Melting point: 83° C.

EXAMPLE 19

(S)-4-(2-Octyloxypyrimidin-5-yl)-phenyl[spiro(1,3-dioxolan-2,1'-cyclohexane)-4-yl]-methyl ether

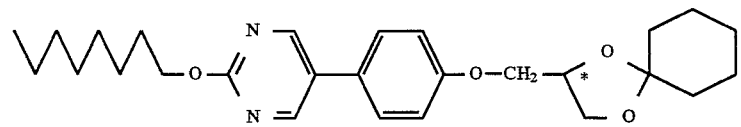

0.72 g of NaH (50% strength solution in paraffin oil) are added to a solution of 3 g of 4-(2-octyloxypyrimidin-5-yl)-phenol in 100 ml of dimethylformamide, and, after the reaction has subsided, 4.89 g of (S)-2,3-O-cyclohexylideneglycerol tosylate are added. After 4 hours 500 ml of $H_2O$ are added, the aqueous mixture is extracted with methylene chloride, and the extract is separated by chromatography ($SiO_2$, 99/1 $CH_2Cl_2$/ethyl acetate). 2.0 g of the desired product, melting point 93.4° C., are obtained after recrystallization from n-hexane.

$[\alpha]_D^{22}$:+8.0 (c=5, $CHCl_3$)

The following are obtained analogously:

EXAMPLE 20

(S)-4-(2-Octylthiopyrimidin-5-yl)-phenyl [spiro(1,3-dioxolan-2,1'-cyclohexane)-4-yl]-methyl ether

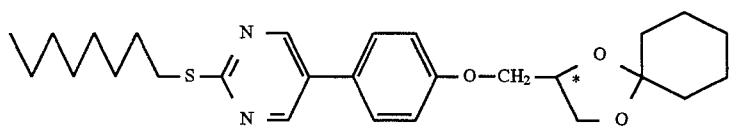

Melting point: 80.2° C. $[\alpha]_D^{22}$:+8.6 (c=5, CHCl$_3$)

EXAMPLE 21

(S)-4-(2-Octylpyrimidin-5-yl)-phenyl [spiro(1,3-dioxolan-2,1'-cyclohexane)-4-yl]-methyl ether

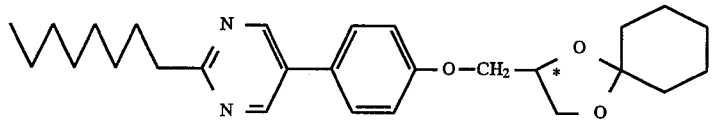

Melting point: 91.3° C. $[\alpha]_D^{22}$:+8.3 (c=5, CHCl$_3$)

EXAMPLE 22

(S)-4-[-<4-(5-Octylpyrimidin-2-yl)-phenoxy>-carbonyloxymethyl]-2,2-dimethyl-1,3-dioxolane

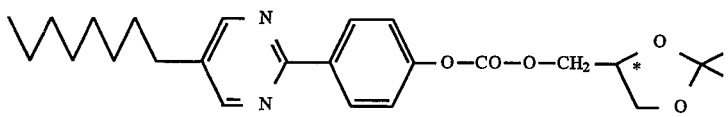

9.9 g of a 15% strength by weight solution of phosgene in toluene are added to a solution of 4.3 g of 4-(5-octylpyrmidin-2-yl)-phenol and 2.1 g of N,N-dimethylaniline in 50 ml of toluene. The mixture is filtered after 24 hours and the filtrate is mixed with 1.2 g of pyridine followed by 2 g of (S)-2,2-dimethyl-1,3-dioxolane-4-methanol, added dropwise at 0° C. After 6 hours the mixture is filtered, the filtrate is freed from solvent in vacuo and the residue is separated by chromatography (SiO$_2$, CH$_2$Cl$_2$). 1.4 g of the desired product, melting point 47° C., are obtained after recrystallization from n-hexane.

$[\alpha]^{22}$:−5.1 (c=1.5, CHCl$_3$)

Method used for determination:

If a small amount of a chiral compound is added to a (non-chiral) solvent, the plane of plane polarized light is rotated through the (characteristic) angle α; this angle is quoted as follows: $[\alpha]_D^T$ (c=x, S), symbols have the following meanings: x=concentration of the solution in g/l, S=solvent, D=589 nm (Na D line) and T=temperature of the solution. The angle of rotation is determined in a polarimeter after the light has traveled through 10 cm.

Use examples A1 to A13

Determination of the HTP (helical twisting power) values, i.e. a measure of the twisting power, is carried out by the method described in Kassubek et al., Mol. Cryst. Liq. Cryst. 8, 305–314 (1969). This is effected by incorporating the chiral doping agents into a nematic host mixture; a planar-oriented wedge cell is filled with this test mixture and the cholesteric helical pitch is determined by measuring the dislocation lines in a polarizing microscope (at a known wedge angle of the cell). The sign of the pitch can be determined by rotating the analyzer.

When the pitch p is known, the HTP is calculated from the equation: HTP=1/p.X, where X is the molar fraction of the chiral doping agent. The amount of host mixtures employed are designated A to D. The HTP values can be seen from Table 1. The host mixtures have the following ranges for the cholesteric phase:

| | |
|---|---|
| A | 78 to 83° C. |
| B | 77 to 98° C. |
| C | 90 to 105° C. |
| D | 61 to 67° C. |

The results show that high HTP values can be obtained, and a wide range of desired pitches is thus made possible by small added amounts of the compounds according to the invention.

TABLE 1

| Use example | Doping agent from example | Host | Molar fraction | Temp (°C.) | p (μm) | HTP (μm$^{-1}$) |
|---|---|---|---|---|---|---|
| A 1 | 1 | A | 0.05 | 78 | −2.6 | −7.7 |
| A 2 | 2 | B | 0.02 | 91 | −5.9 | −8.5 |
| A 3 | 2 | C | 0.02 | 91 | −8.5 | −5.9 |
| A 4 | 5 | D | 0.044 | 66 | −3.2 | −7.1 |
| A 5 | 11 | B | 0.02 | 83 | −42 | −1.2 |
| A 6 | 19 | B | 0.02 | 90 | −6.7 | −7.5 |
| A 7 | 22 | B | 0.02 | 94 | −45 | −1.1 |

For using doping agents for compensating for the pitch of ferroelectric (smectic C*) liquid-crystal mixtures it is advantageous if, even though the twisting power is high, the spontaneous polarization P$_s$ induced simultaneously (in the smectic C* phase) is as low as possible, so that there is then scarcely any need, or no need at all, to take account of the sign compatibility with other chiral mixing components. This is possible when the compounds according to the invention are employed (see Table 2). The P$_s$ values are determined by the Sawyer-Tower method [see K. Skarp et al., Ferroelectric Letters 6, 67 (1986)] at 25° C. in 10% strength by weight test mixtures of the doping agents in the host mixture D (smectic C* phase from 14° to 51° C.); mixtures which can be used in industry should have P$_s$ values of $\geq 5$ nC/cm$^2$, i.e. the desired objective of a low spontaneous polarization has been achieved.

TABLE 2

| Use example | Doping agent from example | Spontaneous polarization $P_s$ (nC/cm$^2$) |
|---|---|---|
| A 8 | 1 | 0.4 |
| A 9 | 3 | <0.2 |
| A 10 | 4 | 0.5 |
| A 11 | 5 | 0.3 |
| A 12 | 11 | <0.2 |
| A 13 | 22 | 2 |

We claim:

1. An optically active 1,3-dioxolane derivative which carries a mesogenic radical in the 4-position and has the formula (I)

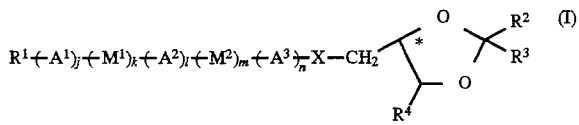

in which the symbols have the following meanings:

$R^1$ is

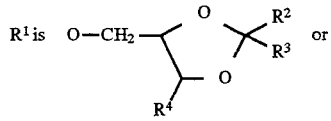

a linear or branched alkyl radical having 1 to 16 carbon atoms or a linear or branched alkenyl radical having 3 to 16 carbon atoms, it being possible for these radicals themselves to contain asymmetric carbon atoms and for one or more non-adjacent —CH$_2$—groups to be replaced by —O—, —S—, —CO—, —O—CO— or —CO—O—, and for one or more H atoms to be replaced by F, $R^2$ and $R^3$ are each an alkyl radical having 1 to 10 carbon atoms, it being possible for one or more H atoms of the alkyl group to be replaced by F, or $R^2$ and $R^3$, together with the C(2) atom of the dioxolane ring, form a cyclopentane, cyclohexane or cycloheptane ring, $R^4$ is H or an alkyl radical having 1 to 10 carbon atoms or an alkenyl radical having 2 to 10 carbon atoms, j and l are zero, 1 or 2, k and m are zero or 1, n is zero, 1 or 2, subject to the following proviso: if j or l are zero, k is zero; if n is zero, m is zero; the total j+l+n is not less than 1 and not more than 3, —$A^1$ and —$A^2$ are

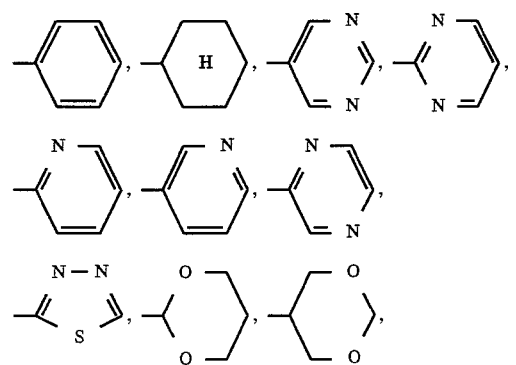

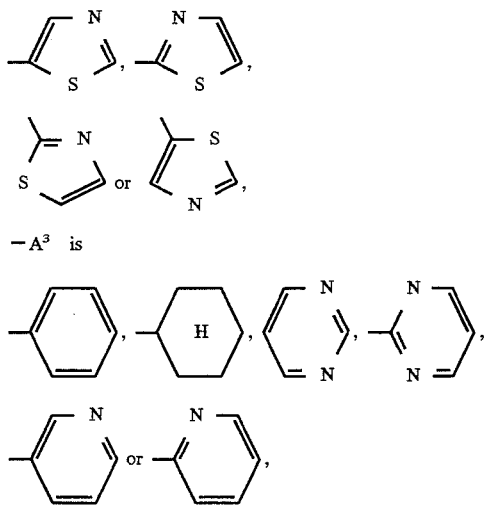

—$A^3$ is

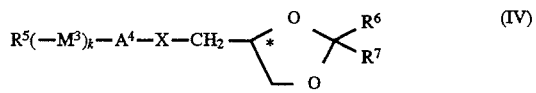

—$M^1$ and —$M^2$ are —CO—O, —O—CO, —CH$_2$CH$_2$, —CH=CH, —CH$_2$O, —OCH$_2$ or —C≡C and X is O or O—CO—O.

2. A 1,3-dioxolane derivative as claimed in claim 1, wherein a derivative of the formula (IV)

$$R^5(-M^3)_k-A^4-X-CH_2 \underset{O}{\overset{O}{\diagdown}} \overset{R^6}{\underset{R^7}{\diagup}} \quad (IV)$$

in which $R^6$ and $R^7$ denote methyl or, together with the C(2) atom of the dioxolane ring, denote a cyclohexane ring, $R^5$ denotes a linear or branched alkyl or alkenyl radical which has 6 to 12 carbon atoms and which can contain an asymmetric carbon atom, X denotes —O— or —O—CO—O—, —$M^3$ denotes —O or —O—CO and —$A^4$ denotes

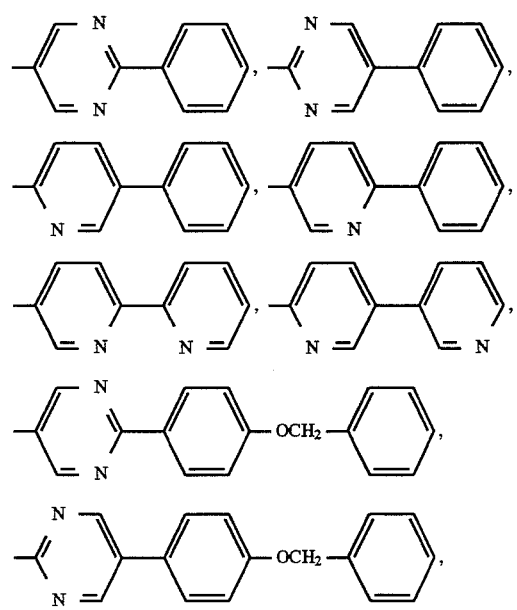

-continued

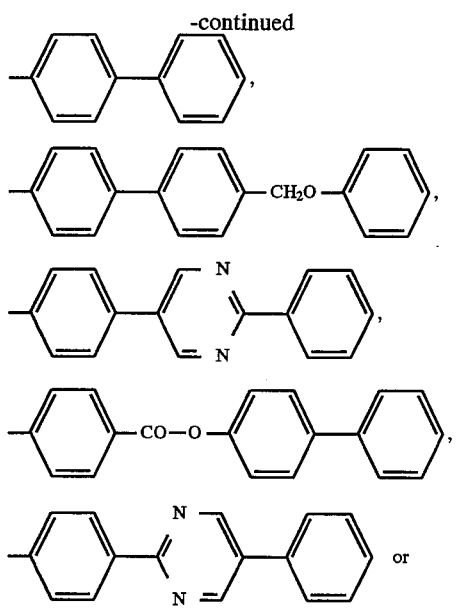

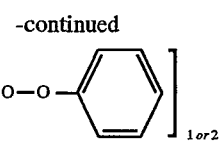

is employed.

3. A liquid-crystal mixture which contains at least one optically active 1,3-dioxolane derivative of the formula (I) as claimed in claim 1.

4. A ferroelectric liquid-crystal mixture which contains at least one optically active 1,3-dioxolane derivative of the formula (I) as claimed in claim 1.

5. A liquid-crystal mixture which contains at least one optically active and mesogenic 1,3-dioxolan-4-yl derivative of the formula (IV) as claimed in claim 2.

6. An electrooptical switching element or display element containing a liquid-crystal mixture as claimed in claim 3.

* * * * *